US007662761B2

(12) United States Patent
Subramanian et al.

(10) Patent No.: US 7,662,761 B2
(45) **Date of Patent: *Feb. 16, 2010**

(54) SOAP BARS COMPRISING INSOLUBLE MULTIVALENT ION SOAP COMPLEXES

(75) Inventors: Vivek Subramanian, Southbury, CT (US); Pravin Shah, Rutherford, NJ (US)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/140,864

(22) Filed: May 31, 2005

(65) Prior Publication Data

US 2006/0270572 A1 Nov. 30, 2006

(51) Int. Cl.
*A61K 7/50* (2006.01)

(52) U.S. Cl. ....................... 510/141; 510/152; 510/153; 510/155

(58) Field of Classification Search ....................... None
See application file for complete search history.

(56) References Cited

U.S. PATENT DOCUMENTS

| | | | | |
|---|---|---|---|---|
| 2,781,321 A | | 2/1957 | Mayhew et al. | |
| 2,988,511 A | | 6/1961 | Mills et al. | |
| 3,030,310 A | | 4/1962 | Turck, Jr. | |
| 3,312,627 A | | 4/1967 | Hooker | |
| 4,574,053 A | * | 3/1986 | Kinsman et al. | 510/141 |
| 5,387,362 A | | 2/1995 | Tollens et al. | |
| 5,540,852 A | | 7/1996 | Kefauver et al. | |
| 5,607,909 A | | 3/1997 | Kefauver et al. | |
| 6,660,699 B2 | * | 12/2003 | Finucane et al. | 510/141 |
| 6,906,023 B1 | * | 6/2005 | Patel et al. | 510/458 |

FOREIGN PATENT DOCUMENTS

| | | |
|---|---|---|
| GB | 791415 | 3/1958 |
| GB | 945062 | 12/1963 |
| WO | 93/02174 | 2/1993 |
| WO | 98/06810 | 2/1998 |
| WO | 98/38269 | 9/1998 |
| WO | 98/53040 | 11/1998 |

* cited by examiner

*Primary Examiner*—Necholus Ogden, Jr.
(74) *Attorney, Agent, or Firm*—Ronald A. Koatz

(57) ABSTRACT

The invention relates to novel bar compositions comprising complexes formed from interaction of multivalent ions and soap. The insoluble complexes permit greater solid contents which counterintuitively, enhance lather (i.e., even if soluble soap is complexed, it is believed more can be used). Further, the complexes enhance rate of wear, hardness, mildness and deposition. The invention further comprises process for enhancing benefits by adding multivalent ions to soap stock during processing.

3 Claims, 2 Drawing Sheets

SOAP BARS COMPRISING INSOLUBLE MULTIVALENT ION SOAP COMPLEXES

FIELD OF THE INVENTION

The present invention relates to solid predominantly soap bars (e.g., 40% to 80% by wt. soap and level of soap exceeds level of synthetic surfactant, if any, by at least 10% by wt.) comprising insoluble multivalent ion soap complexes generated during processing by addition of multivalent cations to soap stock.

BACKGROUND

Soap stock used in the formulation of soap bars is generally comprised of both substantially insoluble, generally longer-chain soaps (e.g., $C_{16}$ or $C_{18}$ palmitic or stearic acid soaps) and more soluble, generally shorter-chain soaps (e.g., $C_{12}$ lauric acid soaps).

The introduction of insolubilizing salts (e.g., the insolubilizing multivalent ion salts of the invention) to precipitate out both the soluble and insoluble soaps found in soap stock according to the common ion effect is not something the person of ordinary skill in the art would consider. In particular, for example, the reduction of soluble soap would be thought to reduce lathering and so there would be no incentive, in fact there would be disincentive, to add such insolubilizing salts.

Unexpectedly, however, applicants have found that the introduction of such multivalent ion salts actually causes the formation of multivalent ion soap complexes (formed from the reaction of multivalent ion and the soluble soap) and produce bars which both lather well and are also unexpectedly milder. Further, the complexes surprisingly enhance deposition of benefit agents, particularly benefit agents (e.g., perfume or other benefit agents solubilized in the soluble soap micelles) which, when in the presence of a greater quantity of soluble soaps, would more readily wash away.

U.S. Pat. No. 5,607,909 to Kafauver et al. discloses personal cleansing freezer bars containing 5-35% magnesium soaps. The multivalent ions claimed for use in the subject application specifically excludes magnesium.

U.S. Patent Publication No. WO 98/06810 to Hauwermeiren et al., discloses laundry detergent compositions having filler salts selected from alkali and alkaline earth metal sulfates and chlorides (sodium sulfate is a preferred filler). PCT Publication WO 98/38269 to Ramanan et al., discloses a laundry detergent bar with improved physical properties resulting from the formation of a complex of calcium and siliceous material in situ. WO 98/53040 to Ramanan discloses laundry bar with improved sudsing and physical properties having a metal anionic sulfonate surfactant complex.

All the above are laundry compositions and are not personal wash bar compositions comprising 40% to 80% soap wherein soap exceeds level of synthetic, if any, by at least 10% by wt. Further, as laundry bars, the compositions comprise builders (e.g., phosphate or other builders) and/or enzymes. Compositions of the subject invention comprise less than 2%, preferably less than 1% by wt. builder, if any, and preferably are substantially free of builders. Further the compositions of the subject invention are substantially free of enzymes, since such enzymes would not be used in personal wash compositions.

U.S. Pat. No. 6,660,699 to Finucane et al., discloses the use of inorganic salts, e.g., calcium chloride, as latent acidifiers in bars comprising both soaps and synthetic surfactants. These latent acidifier salts remain as salts in the bar even after bar processing and do not react with fatty acid soaps or other alkaline material in the bar to form free fatty acid during bar formation. It is only as the bar is used/diluted in water that the latent acidifiers neutralize harsh soap or other alkaline materials in the bar, or reduce pH of bar through other acid-base interaction, to create mild cleansing action.

By contrast, the salts added in the composition of the invention do in fact predominantly react during bar processing (i.e., with soluble short-chain complexes) to precipitate insoluble soap complexes in the final bar. The increase in solid content (from the formation of insoluble soap complexes) allows the use of higher levels of other ingredients like mild syndets, oils or short chain fatty acids (i.e., normally too much of these components make bars too mushy and/or not hard enough for good processing). Thus, the insoluble complexes allow more of such above named ingredients to be used without compromising hardness while at the same time introducing the benefit associated with these ingredients, i.e., enhanced lather. Moreover, the reduction in solubility (again due to the insoluble complexes) enhances deposition by preventing benefit agents which would normally be washed away with the soluble soap from being so readily washed.

BRIEF SUMMARY OF THE INVENTION

The present invention relates to predominantly soap bar (e.g. 40% to 80% by wt. soap and level of soap exceeds level of synthetic; bars preferred contain less than about 5%, preferably less than about 3% by wt. synthetic surfactant and preferably less than about 5% by wt. anionic) wherein the bar contains levels of insoluble multivalent metal soap complex of at least 8% to about 60%.

The complex can be measured using pulsed $H^1$ FT-NMR spectroscopy (proton relaxation) as described in detail later in the specification.

In a second aspect of the invention, the invention relates to a process for enhancing lather (through addition of more "soluble soaps than normally possible), enhancing mildness (because harsh soap is not solubilized, but rather is precipitated into complexes) and of enhancing deposition (because benefit agent solubilized in the micelles is not as readily washed away), which process comprises adding multivalent ions of the form $M^{n+}$, where n is a valence greater than 1, so that the amount of the insoluble—soap complex is at least 8% (e.g., about 8% to 60%) and M is anion other than $Mg^{2+}$.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION

Figure 1:
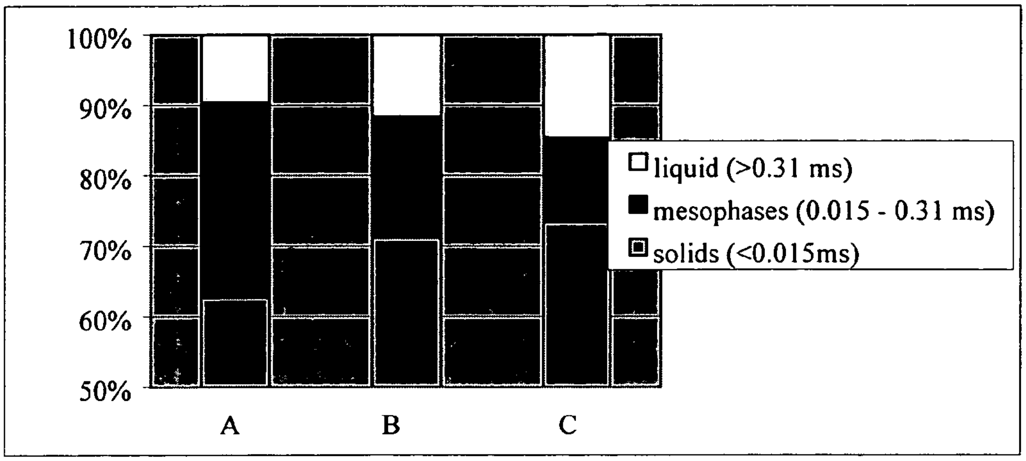
FIG. 1 shows % of solids, liquids and mesophases in compositions where multivalent ion soap complex is formed (i.e., from use of multivalent salts).

The subject invention relates to predominantly soap bar compositions (further comprising less than 5%, preferably less than 3% by wt. synthetic) comprising complexes formed from the interaction of multivalent cations and soluble shorter-chain soap normally found in predominantly soap bars. The compositions are also preferably substantially free of builders and of enzymes. Unexpectedly, applicants have found that these complexes form (upon addition of the multivalent cation) and lead, rather than to loss of user properties (which might be expected from the reduction in soluble soap), to enhanced user properties like more lather, longer rate of wear and benefit agent deposition.

Specifically, the invention comprises soap bar composition comprising:

a) 40% to 80% by wt. fatty acid soap;
   wherein the level of soap exceeds the level of synthetic surfactant, if any (preferably less than about 5% by wt., preferably less than about 3% by wt. synthetic and less than about 5% anionic surfactant);
b) 0% to 30% by wt. structurant (e.g., free fatty acid, polyalkylene glycol);
c) 5% to 25% water;
   wherein 8% to 60% of said bar comprises a complex formed from the interaction of soluble shorter-chain soap and multivalent ion (e.g., multivalent cation salt).

The bar is generally made by conventional processing including mixing, milling, plodding and stamping without compromising bar structure (using, for example, cheesewire measurements of bar hardness).

Bar compositions are also, in preferred embodiments, substantially free of builder(s) and substantially free of enzyme.

In a second embodiment of the invention, the invention relates to a process for enhancing lather, mildness and/or deposition which process comprises adding multivalent ions to a mix (mixed, for example, using a Z-blade mixture) to form a multivalent ion-soap complex. Water (if necessary) and multivalent (e.g., $CaCl_2$) are added to soap noodles in the mixer and mixed for about 20 minutes at about 30-35° C. Whenever other additives (e.g., coco fatty acid or synthetic detergents) are in the formulation, they are added after the above mixing step for about an additional 20 minutes. This is followed by milling and extruding at about 30-35° C.

The term "soap" is used here in its popular sense, i.e., alkali metal or alkanol ammonium salts of alkane or alkene monocarboxylic acids. The term "soap" is used here in its popular sense, i.e., the alkali metal or alkanol ammonium salts of aliphatic alkane- or alkene monocarboxylic acids. Sodium, potassium, mono-, di and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkanoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. The proportion will be greater when mixtures of coconut oil and fats such as tallow, palm oil or non-tropical nut oils or fats are used, wherein the principle chain lengths are $C_{16}$ and higher. Preferred soap for use in the compositions of this invention has at least about 85% fatty acids having about 12-18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are general exemplified by the tropical nut oils of the coconut oil class. For instance, they include: palm kernel oil, babassu oil, ouricuri oil, tucum oil, cohune nut oil, muru-muru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil in which case the fatty acid content is about 85% of C12-C18 chain length. The fatty acids soaps of the invention may also comprise a mixture of $C_{16}$-$C_{24}$ long chain length and $C_8$-$C_{24}$ short chain lengths soaps.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$) or staric ($C_{18}$) acids with an alkali metal hydroxide or carbonate.

As noted, the soap exceeds level of synthetic surfactant, if any by at least 10% by wt. Typically, there will actually be less than about 5% by wt. synthetic, preferably less than about 3% and sometimes no synthetic. If present, synthetic will comprise less than about 5% anionic, preferably less than about 3%.

If present synthetic can be selected from the group consisting of anionic, nonionic, cationic, zwitterionic amphoteric surfactants and mixtures thereof.

Structurant

In general, bars of the invention may comprise 0 to 40%, preferably 5 to 35% by wt structurant (e.g., free fatty acid, water soluble structurant, glycerol monoalkanoate noted below). Preferably, the bar will contain 5% to 30% structurant though none is required.

Free Fatty Acid

The standard may be free fatty acids of 8-22 carbon atoms may also be desirably incorporated within the compositions of the present invention. These fatty acids may also operate as superfatting agents and as skin feel and creaminess enhancers. Superfatting agents enhance lathering properties and may be selected from fatty acids of carbon atoms numbering 8-18, preferably 10-16, generally in an amount up to 15% by weight (although higher amounts may be used) of the composition. Skin feel and creaminess enhancers, the most important of which is stearic acid, are also desirably present in these compositions.

Water Soluble Structurant

Another compound which may be used in the bar is water soluble structurant (e.g., polyalkylene glycol).

This component should comprise 0% by wt. to 25%, preferably greater than 5% to 20% by wt. of the bar composition.

The structurant (e.g., polyalkylene glycol) has a melting point of 40° C. to 100° C., preferably 45° C. to 100° C., and more preferably 50° C. to 90° C.

Materials which are envisaged as the water soluble structurant (b) are moderately high molecular weight polyalkylene oxides of appropriate melting point and in particular polyethylene glycols or mixtures thereof.

Polyethylene glycols (PEG's) which may be used may have a molecular weight in the range 400 to 20,000.

It should be understood that each product (e.g., Union Carbide's Carbowax® PEG 8,000) represents a distribution of molecular weights. Thus PEG 8,000, for example, has an average MW range of 7,000-9,000, while PEG 300 has an average MW range from 285 to 315. The average MW of the product can be anywhere between the low and high value, and there may still be a good portion of the material with MW below the low value and above the high value.

In some embodiments of this invention it is preferred to include a fairly small quantity of polyalkylene glycol (e.g., polyethylene glycol) with a molecular weight in the range from 5,000 to 50,000, especially molecular weights of around 10,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a larger quantity of other water soluble structurant (b) such as the above mentioned polyethylene glycol of molecular weight 400 to 20,000.

Some polyethylene oxide polypropylene oxide block copolymers melt at temperatures in the required range of 40° C. to 100° C., and may be used as part or all of the water soluble structurant (b). Preferred ere are block copolymers in which polyethylene oxide provides at least 40% by weight of the block copolymer. Such block copolymers may be used in mixtures with polyethylene glycol or other polyethylene glycol water soluble structurant.

Glycerol Monoalkanoate

Another optional structurant which may be used is glycerol monoalkanoate wherein alkanoate group may be $C_{12}$-$C_{24}$ alkyl (e.g., glycerol monostearate). This may comprise 0-30% by wt. of bar, preferably 5% to 25% by wt.

Water

The bar compositions of the invention comprise about 5 to 25%, preferably 5 to 16% water.

Complex

The complex of the invention is formed from a combination of multivalent ion and generally, soluble shorter chain (e.g., C8 to C14 saturated) or soluble unsaturated (e.g., oleic acid) soaps. By soluble is typically meant that at least 1 wt. % level of soap will dissolve in water at less than 40° C.

The multivalent ion typically is a calcium or other Group II metal complex (e.g., calcium chloride), but magnesium multivalent salts are specifically excluded.

The complex will form about 8% to about 60% of the bar compositions, preferably 8to 50%.

The bar compositions of the invention are not laundry bars and will comprise less than 2%, preferably less than 1%, if more preferably have substantially no builder. Further, as personal wash compositions, they will comprise substantially no enzyme.

EXAMPLES

The following protocols were used to measure wear rate (measure of bar "mushiness") and zein solubility (measure of bar harshness or mildness).

Procedure for Rate of Wear

1. Record the weight of each bar prior to being washed.
2. Adjust the faucet water to 105° F. (40° C.) and keep it running into the bucket.
3. Immerse the bar and hands into the bucket.
4. Remove the bar from the water and rotate twenty (20) half turns.
5. Repeat steps 3 and 4.
6. Immerse the bar for a third time and place into a soap dish.
7. Add 7.5 ml of water to the soap dish.

8. Repeat the wash procedure (steps 2 through 4) three additional times during the first day. The washes should be spaced evenly throughout the work day.
9. After the last wash of the day, add 7.5 ml of water to the soap dish and let the bar sit overnight.
10. The following morning repeat the wash procedure (steps 2 through 4) then place the bar sideways on a drying rack.
11. Allow the bar to sit for 24 hours then weigh the bar to the nearest 0.01 g.

Calculation

Wear Rate (gm/wash) equals initial weight−final weight.

Procedure for Zein Solubility

1. Using the flat edge of a spatula, shave the surface of the bar into ribbons.
2. Mix 2.5 gram bar ribbons with 97.5 gram distilled and deionized Milli-Q water.
3. Sonicate above mixture for 1 minute and leave it in a 50° C. oven for 15 minutes. Shake the mixture frequently.
4. Mix 5 gram zein protein in 80 gram bar solution from step 3. Leave the mixture in room temperature for 24 hours. Vigorously shake the mixture once for a awhile.
5. Use a1 mL syringe to take out the solution part of the mixture and filter the solution through a syringe filter with 0.45 μm Nylon membrane.
6. Filter the solution from step 5 again through a syringe filter with 0.45 μm Nylon membrane.
7. Dilute filtered solution with distilled and deionized Milli-Q water by 100 times (0.1 gram filtered solution dissolved in 10 gram water).
8. The concentration of the zein in the diluted filtered solution is determined using a UV-V is spectrophotometer in the range of 200 nm<λ<350 nm at a scanning rate of 800 nm/min. The absorption intensity at wave length λ=278 nm is recorded for the calculation of the zein concentration ($C_1$).
9. The zein solubility in the 2.5 wt./wt. % bar solution is therefore $C_1$ multiplied by the dilution times.

After 24 hours equilibrium, observe the sample to make sure there is undissolved solid zein remaining in the sample. Otherwise, add more zein into the solution and equilibrium for another 24 hours to make sure that excessive zein is added into the solution.

Procedure for Measuring Lather

Apparatus

Toilet bars 2 large sinks measuring funnel

The measuring funnel is constructed by fitting a 10½ inch diameter plastic funnel to a graduated cylinder which has had the bottom cleanly removed. Minimally the graduated cylinder should be 100 cc's. The fit between the funnel and the graduated cylinder should be snug and secure.

Procedure

Before evaluations proceed, place the measuring funnel into one of the sinks and fill the sink with water until the 0 cc mark is reached on the graduated cylinder.

1. Run the faucet in the second sink and set the temperature to 95° F. (35° C.).
2. Holding the bar between both hands under running water, rotate the bar for ten (10) half turns.
3. Remove hands and bar from under the running water.
4. Rotate the bar fifteen (15) half turns.
5. Lay the bar aside.
6. Work up lather for ten (10 seconds.
7. Place funnel over hands.
8. Lower hands and funnel into the first sink.
9. Once hands are fully immersed, slide out from under funnel.
10. Lower the funnel to the bottom of the sink.
11. Read the lather volume.
12. Remove the funnel with lather from the first sink and rinse in the second sink.

The test should be performed on 2 bars of the same formulation, same batch etc. and the volume should be reported as an average of the 2 assessments.

Procedure for Measuring Yield Stress

Calculation

Yield stress results are typically reported in kPa. A 200 gm weight is utilized and cheese-wire having a diameter was 0.5 mm.

It is important that the cheese-wire diameter be checked periodically as thickness deviation may result in an unreliable calculation.

Stress is calculated as follows:

$$\text{Yield Stress} = 0.000368 \times \frac{W}{L \times d} Nm^{-2} \times 10^5$$

$$W = \text{weight (gm)}$$
$$L = \text{length of the slice (cm)}$$
$$d = \text{diameter of the wire (cm)}$$

Cheese-wire data is often reported as kPa N $m^{-2} \times 10^5$=Pa× $10^5$=100 kPa.

Therefore, when using a 200 gm weight, and a wire diameter of 0.5 mm, the following conversion factor is applicable:

$$\frac{147.2}{L} \text{ Units reported as } kPa$$

Examples 1-3

In order to show that the addition of multivalent salt (e.g., calcium chloride, $CaCl_2$) forms a complex with soap which actually enhances solids formation (despite increased moisture due to use of dihydrate salt applicants conducted the following experiment.

The samples for the experiment were prepared as follows. Soap noodles (85/15 tallow/nut oil) were reacted with different levels of $CaCl_2$ at room temperature (e.g., about 20° C.) in a 10 g Z-blade mixer for 25 minutes. Following this, the moisture content in the noodles was measured using the Karl Fisher method. The samples and their moisture content are listed in the following table. The samples containing $CaCl_2$ have higher moisture because the salt used was a dihydrate salt.

TABLE 1

| Sample | 85/15 noodles | $CaCl_2$ (anhydrous) | $H_2O$ |
|---|---|---|---|
| 1 | 86.68 | 0.00 | 13.32 |
| 2 | 80.15 | 3.00 | 16.85 |
| 3 | 75.85 | 6.00 | 18.15 |

In the pulsed NMR experiment, proton relaxation data are collected using a Bruker Model NMS 120 Minispec equipped with a 0.5 T magnet. The operating frequency was 20 MHz. The decay curve was fitted to a series of Gaussian and exponential functions with decay times characteristic for solid, liquid crystalline (mesophases), and liquid phases. The form of the decay curve and the relaxation times ($T_2$) associated with different phases is well known in literature. For typical solids, the decay follows a Gaussian function with a $T_2$ in the range of 12-15 μs, whereas for liquid crystalline (mesophase) and liquid materials the decay curve is exponential with $T_2$ in the range of a few hundred μs and $10^5$ μs respectively. This is seen from FIG. 1 and from Table 2 below.

TABLE 2

| Example | Solids % (<0.015 ms) | Mesophases % (0.015-0.31 ms) | Liquids % (<0.31 ms) |
|---|---|---|---|
| 1 | 62.7 | 27.7 | 9.6 |
| 2 | 71.2 | 17.1 | 11.7 |
| 3 | 73.4 | 12 | 14.6 |

Control: 85/15 Bar (e.g., 85% tallow oil and 15% coconut oil)

Example 4: 85/15+10% $CaCl_2$+20% SASOLFIN23 (synthetic detergent).

Figure 2:
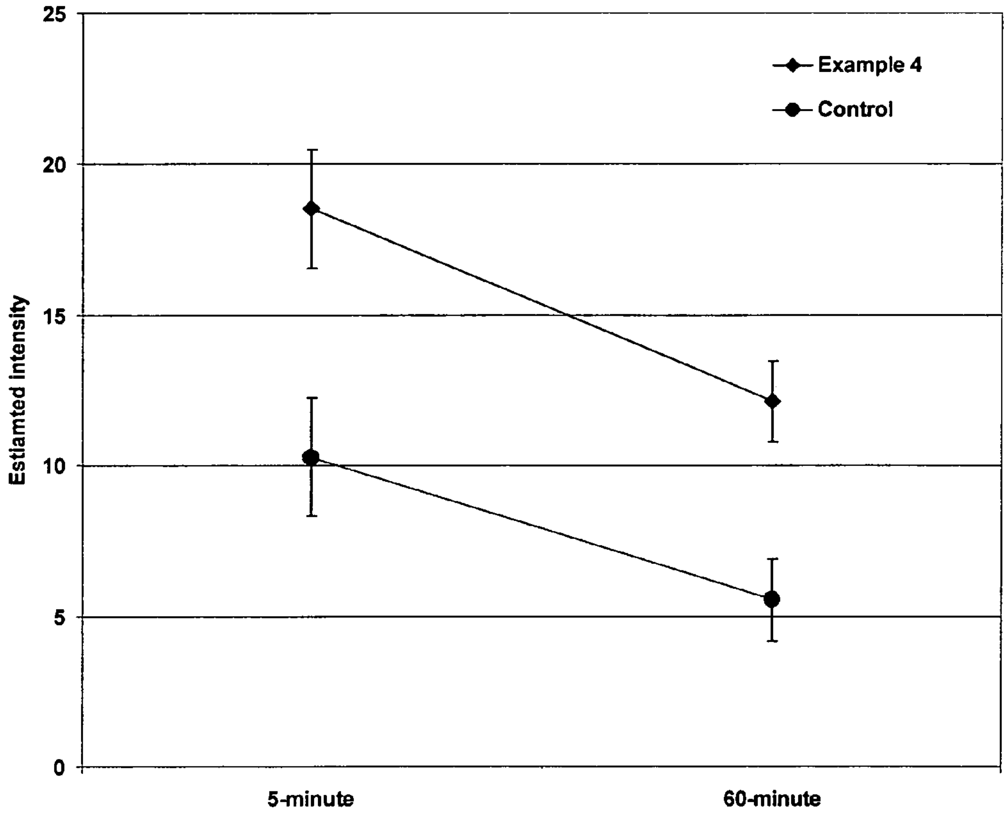
FIG. 2 shows enhanced perfume intensity/deposition as a function of multivalent salt used.

FIG. 2 shows the results of a perfume panel 5 minutes and 60 minutes post wash.

It can be seen that for the $CaCl_2$ bar (Example 4) the perfume intensity is higher at both time points suggesting that the $CaCl_2$ prototype is more efficient at depositing perfume.

As noted, FIG. 2 shows how estimated intensity is higher at two measured points for the Examples versus comparative. The increased intensity is a direct function of the enhanced deposition.

Shown below are the results of a perfume panel 5 minutes and 60 minutes post wash. It can be seen that, for the $CaCl_2$ bar, the perfume intensity is higher at both time points suggesting that the $CaCl_2$ prototype is more efficient at depositing perfume.

Examples 5-9

The following set of example show the effect of $CaCl_2$ (multivalent salt) on the mildness, lather, rate of wear and bar hardness.

| Examples | $CaCl_2$ (%) | Coconut fatty acid (%) | Moisture | Yield Stress (kPa) | Zein (%) | ROW (g/wash) | Lather (ml) |
|---|---|---|---|---|---|---|---|
| 5 | 0 | 0 | 12 | 200 | 4.57 | 1.1 | 55 |
| 6 | 1 | 10 | 12 | 73.6 | | 0.79 | 55 |
| 7 | 2 | 10 | 12 | 113 | | 0.67 | 78 |
| 8 | 3 | 10 | 12 | 113 | | 0.48 | 85 |
| 9 | 5 | 10 | 12 | 130 | 2.88 | 0.56 | 53 |

Specifically, Table 2 and FIG. 1 show the fraction of protons which are associated with the solid, liquid and liquid crystalline phase (mesophase) of the noodles. It can be seen clearly that despite the increasing moisture content of the samples (i.e., for example 2 and 3 versus Example 1), the solids content is higher in the presence of $CaCl_2$ suggesting that some, if not all, of the soap has reacted to form an insoluble soap metal ion complex. More precisely, the data suggests that with sample 2, at least 8.5% of the mesophases present in 1 is converted to solids (e.g., 62.7 to 71.2% solids).

Example 4 & Control

In order to show enhanced perfume deposition, applicants tested the perfume intensity of a standard 85/15 control bar and same bar containing 10% $CaCl_2$ and 20% anionic surfactant (e.g., Sasolfin 23) at two different points. The bar compositions are noted below.

The following set of examples show enhanced perfume deposition from a bar containing high levels of $CaCl_2$:

The first column is the $CaCl_2$ level, second is the level of coconut fatty acid and the third is the moisture content in the formulation. The fourth column represents yield stress in kPa as measured by the cheesewire test. Generally, a yield stress of 100 is considered to be acceptable for conventional processing. It can be seen that all formulations, except Example 6, pass this criterion. The zein scores, which is the amount of zein protein solubilized is a measure of the mildness of the bar. The value of 2.88 for Example 9 indicates a very mild bar. The ROW (rate of wear) data suggests that the $CaCl_2$ containing bars are superior (lower values wear more slowly) indicating that the insoluble soap-metal ion complex produces bars which wear less than conventional bars. Finally, the lather from bars containing between 2-3% $CaCl_2$ is seen to be higher than the others. This is again unexpected. Apparently, formation of complex allows more soluble soap (responsible for lather) than would normally be found, thereby enhancing lather.

The invention claimed is:

1. A bar composition consisting essentially of:

(a) 40 to 80% by wt. fatty acid soap;

(b) less than 3% by wt. synthetic surfactant;

(c) 5 to 30% by wt. structurant selected from the group consisting of free fatty acids, polyalkylene oxides, glycerol alkanoates and mixtures thereof; and (d) 5 to 16% by wt. water;

wherein 8 to 60% by wt. of said bar comprises a complex formed from the interaction of soluble soap and multivalent ion, said soluble soap being saturated $C_8$ to $C_{14}$ soap and/or unsaturated soap;

wherein composition comprises less than 2% by wt. builder;

wherein compositions is substantially enzyme free;

wherein said multivalent ion does not comprise magnesium;

wherein soap and multivalent ion are added before addition of synthetic surfactant, if any; wherein a chloride of the multivalent ion is reacted with soap noodles and optional water at 30-35° C. to form said complex directly as part of the soap solid formation process.

2. A bar composition according to claim 1, wherein fatty acid soap comprises mixture of $C_{16}$ to $C_{24}$ long chain length $C_8$-$C_{14}$ and short chain length soaps.

3. A process to enhance lather, mildness, rate of wear and hardness in the bar of claim 1 which process comprises adding complex inducing multivalent ion to the fatty acid soap to form multivalent ion-soap complex prior to addition of synthetic surfactant, if any.

* * * * *